United States Patent [19]
Filoso et al.

[11] Patent Number: 5,879,352
[45] Date of Patent: Mar. 9, 1999

[54] OSTEOSYNTHETIC LONGITUDINAL ALIGNMENT AND/OR FIXATION DEVICE

[75] Inventors: Silvano Filoso; Robert Frigg, both of Davos-Platz, Switzerland

[73] Assignee: Synthes (U.S.A.), Paoli, Pa.

[21] Appl. No.: 877,037

[22] Filed: Jun. 17, 1997

Related U.S. Application Data

[63] Continuation-in-part of Ser. No. 323,020, Oct. 14, 1994, abandoned.

[51] Int. Cl.$^6$ .................................................. A61B 17/72
[52] U.S. Cl. .................................................. 606/62; 606/60
[58] Field of Search ................................. 606/62, 63, 64, 606/60, 72, 86

[56] References Cited

U.S. PATENT DOCUMENTS

| | | | |
|---|---|---|---|
| 5,034,012 | 7/1991 | Frigg | 606/62 |
| 5,180,382 | 1/1993 | Frigg et al. | 606/72 |

FOREIGN PATENT DOCUMENTS

| | | |
|---|---|---|
| 517435 | 12/1992 | European Pat. Off. . |
| 26 57 303 | 6/1977 | Germany . |
| 967 478 | 10/1982 | U.S.S.R. . |
| 1 111 748 | 9/1984 | U.S.S.R. . |
| WO-A-9313713 | 7/1993 | WIPO . |

OTHER PUBLICATIONS

Synthes booklet entitled "Universal Tibial and Femoral Nail System", Institut Straumann AG, Jan. 1988, Switzerland.

*Primary Examiner*—Guy V. Tucker
*Attorney, Agent, or Firm*—Fish & Richardson P.C.

[57] ABSTRACT

An osteosynthetic alignment or fixation device has a flexible mode making it more easily positioned and a rigid mode in which it provides a desired measure of support in a desired shape to a fractured or deformed bone.

31 Claims, 11 Drawing Sheets

OSTEOSYNTHETIC LONGITUDINAL ALIGNMENT AND/OR FIXATION DEVICE

This application is a continuation-in-part of our application, U.S. Ser. No. 08/323,020, filed Oct. 14, 1994, now abandoned.

FIELD OF THE INVENTION

This invention relates to an osteosynthetic longitudinal alignment or fixation device, in particular to an intramedullary nail, capable of assuming a flexible mode, enabling it to be more easily applied to the bone to be treated, and a rigid mode, enabling it to provide the support required.

BACKGROUND OF THE INVENTION

Intramedullary nails have found widespread use in osteosynthesis. Since the first application of this method by K ÜNTSCHER, intramedullary nails have been developed to include a wide range of indications (locking, gamma nail, reconstruction nail).

Despite the wide range of development, the basic concept has remained unchanged. It involves introducing a hollow or solid cylinder into the intramedullary cavity of a tubular bone. In early days nailing of the femur was predominant, but with time this type of osteosynthesis has been applied to all major long bones. Because the intramedullary canals of the various long bones have been prepared by reaming out the medullae with reamers no particular attention has been paid to nail configuration or profile.

Conventional intramedullary nails are typically rigid, stiff and relatively straight. As a result, the insertion points of the nail into the bone are usually fixed and are determined by the geometries of the nail and the medullary canal. However the points selected for insertions of rigid intramedullary nails may have drawbacks for reasons of anatomy and accessibility:

significant muscle coverage over insertion site may make the insertion point difficult to approach surgically and may, as well, lead to soft tissue damage as the surgeon tries to approach the insertion site;

possible interference with joint areas possible damage to the opposite cortex caused upon entry of the rigid nail tip into the medullary canal;

risk of damage to bone at the insertion site due to excess stress during insertion of nail (caused by too rigid nails);

the insertion site and nail path created by a rigid intramedullary nail in a long bone may interfere with the growth plate in your patients.

An intramedullary nail having a flexible conformation which can be stiffened after insertion of the nail into the medullary cavity is disclosed in SU 1111-748-A. The drawback of this nail lies in the fact that its single segment has end teeth and knurled surfaces forming pairs of locking joints so that upon stiffening the nail takes on the shape of the intramedullary cavity irrespective of the possible presence of a displaced fracture.

Another aspect is the geometry of the nail cross section. If one is concerned with causing the least damage to the intramedullary cavity and preserving blood circulation in the bone, the nail cross section has to be taken into consideration more seriously. This is particularly true for the nailing of the humerus. The intramedullary cavity of the humerus is not circular over its entire length, and therefore the axially off-set insertion of a nail with a circular profile is not recommended.

SUMMARY OF THE INVENTION

The present invention is designed to overcome foregoing problems by providing a fixation or alignment device, particularly an intramedullary nail, which is capable of assuming a flexible mode in which it is more easily adapted to insertion or positioning in or adjacent the bone to be treated and a rigid mode, in which it provides the desired support.

Specifically, the invention provides an osteosynthetic fixation or alignment device comprising an upper end segment, a lower end segment and a plurality of intermediate segments, each of said segments having upper and lower ends and a longitudinal axis, connecting means joining said segments end to end and tightening means for pressing said segments together into a rigid configuration, the abutting ends of at least two of said segments being shaped so that when tightened, the device assumes a predetermined shape.

An intramedullary nail according to the invention can be inserted in its flexible state through insertion points which are more accessible in terms of soft tissue coverage and over-all location. The insertion point is not fixed and can be chosen according to anatomical factors so as to avoid problems of the traditionally rigid intramedullary nails leading to soft tissue damage and interference with joints. As the nail is inserted into the medullary canal, it bends to fit into and conform to the canal.

In a nail according to the invention the segments can either be directly linked together, e.g. by special laser-cut geometry of their ends, springs etc., or alternatively the segments can be separate pieces connected by means of another separate part, e.g. by a cable, wire or similar connecting device.

A principal advantage of a nail according to the invention lies in the fact that it can be stiffened to a pre-determined shape and not necessarily to the configuration which the nail has temporarily adopted upon insertion in the medullary cavity. Thus the bone fragments may be forced to conform to the pre-determined shape of the stiffened nail and to become aligned as desired. In this way a displaced fracture can be corrected.

Further advantages of devices according to the invention are the following:

The insertion point is not fixed and can be chosen according to anatomical factors so as to avoid soft tissue damage and interference with joints and growth plates;

anterograde and retrograde approach may both be possible;

there is less risk of damage to the bone at the insertion point and at the inner cortex during insertion;

it may be used on young patients by simply avoiding the growth plates during introduction and insertion of the nail into the medullary cavity.

While one of the principal applications of the invention is as an intramedullary nail, the invention can also be applied to extramedullary devices, e.g. bone plates, longitudinal rods for spinal fixation systems, longitudinal bars for external fixation apparatus and similar osteosynthetic devices where it is desirable to have a longitudinal element which is flexible during anchoring to the bone but which can be reversible stiffened at any moment to take a pre-determined shape.

BRIEF DESCRIPTION OF THE DRAWINGS

The invention will be further described with reference to the accompanying drawings in which.

DETAILED DESCRIPTION OF THE INVENTION

Figures 1, 2:
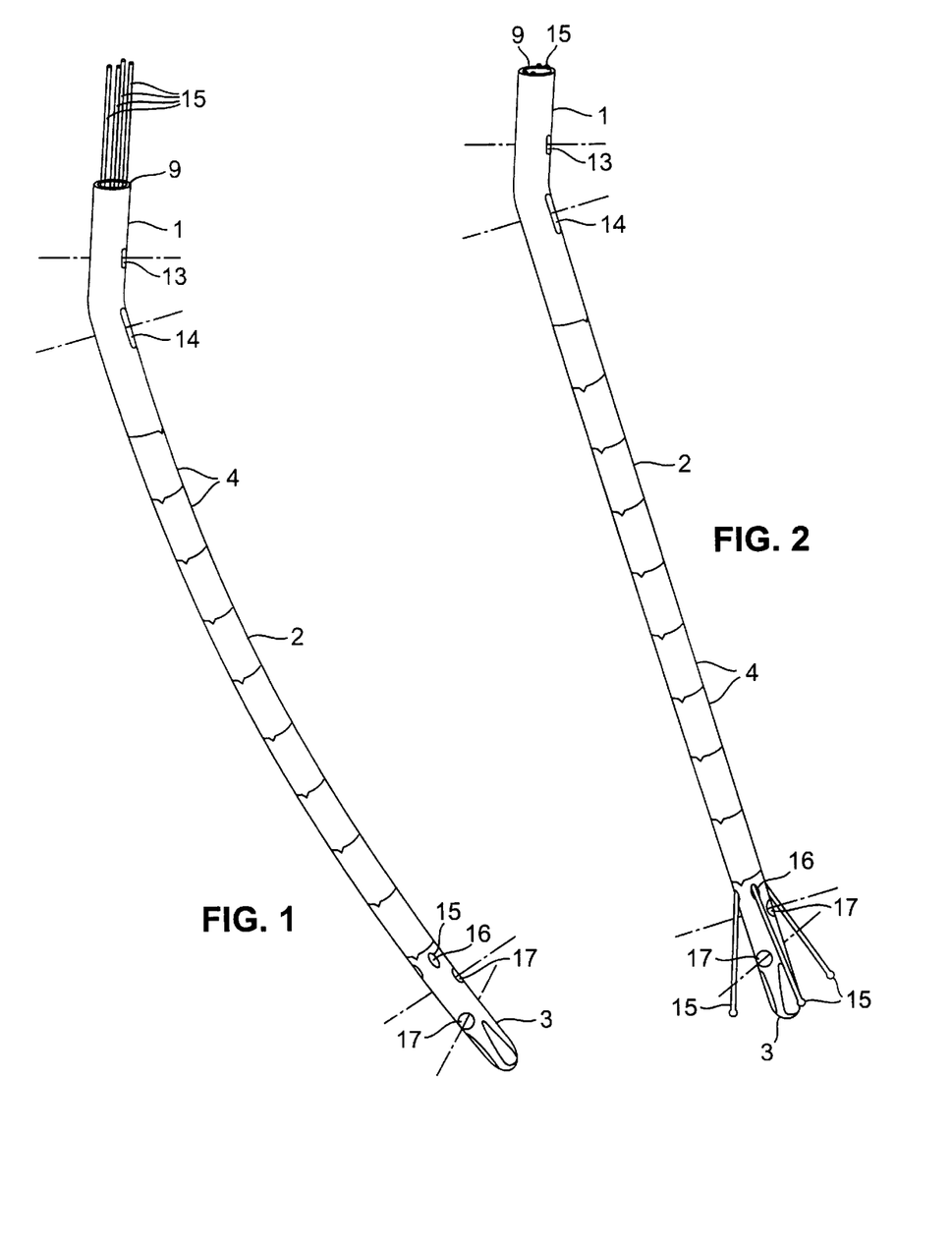
FIG. 1 is a perspective view of a nail according to the invention in the flexible state.
FIG. 2 is a perspective view of the nail according to the invention in the rigid state.
Figure 1A:
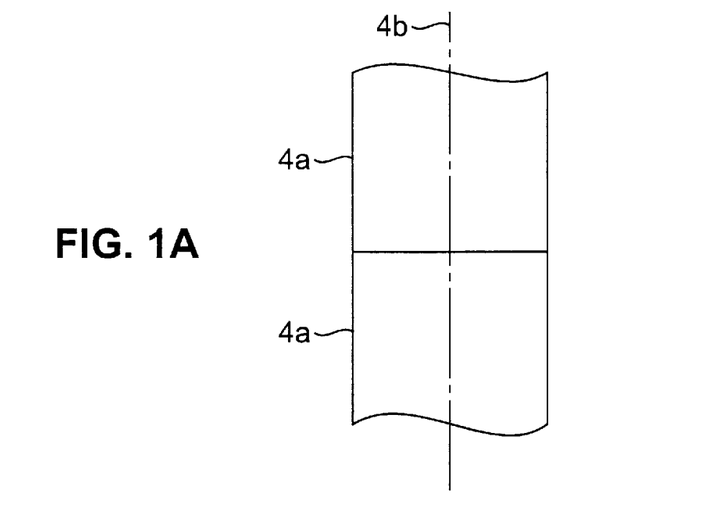
FIG. 1A is a front elevational view illustrating a pair of segments of a nail according to the invention in which the abutting ends are perpendicular to the longitudinal axis.
Figure 1B:
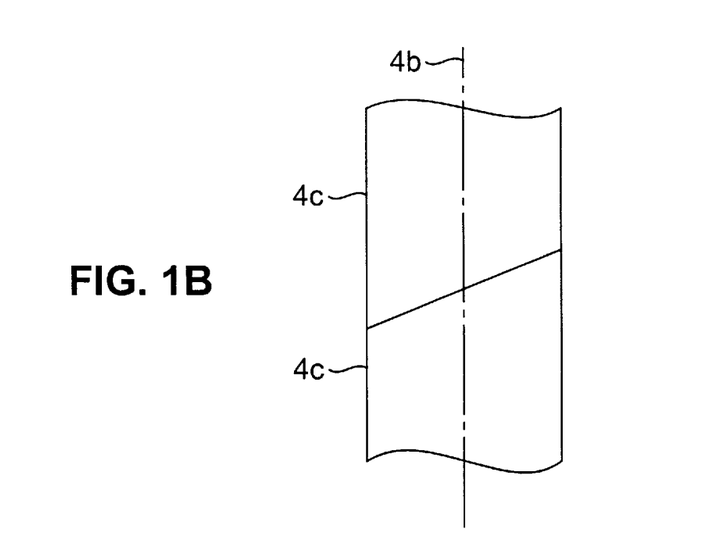
FIG. 1B is a front elevational view of a pair of segments in a nail according to the invention in which the ends of the adjacent segments meet at an angle other than 90° to the longitudinal axis.

Referring to FIGS. 1 and 2, an intramedullary nail according to the invention comprises an upper end segment 1, a lower end segment 3 and a central portion 2 comprising a plurality of longitudinally arranged intermediate segments 4.

Figures 3, 6, 7, 8:
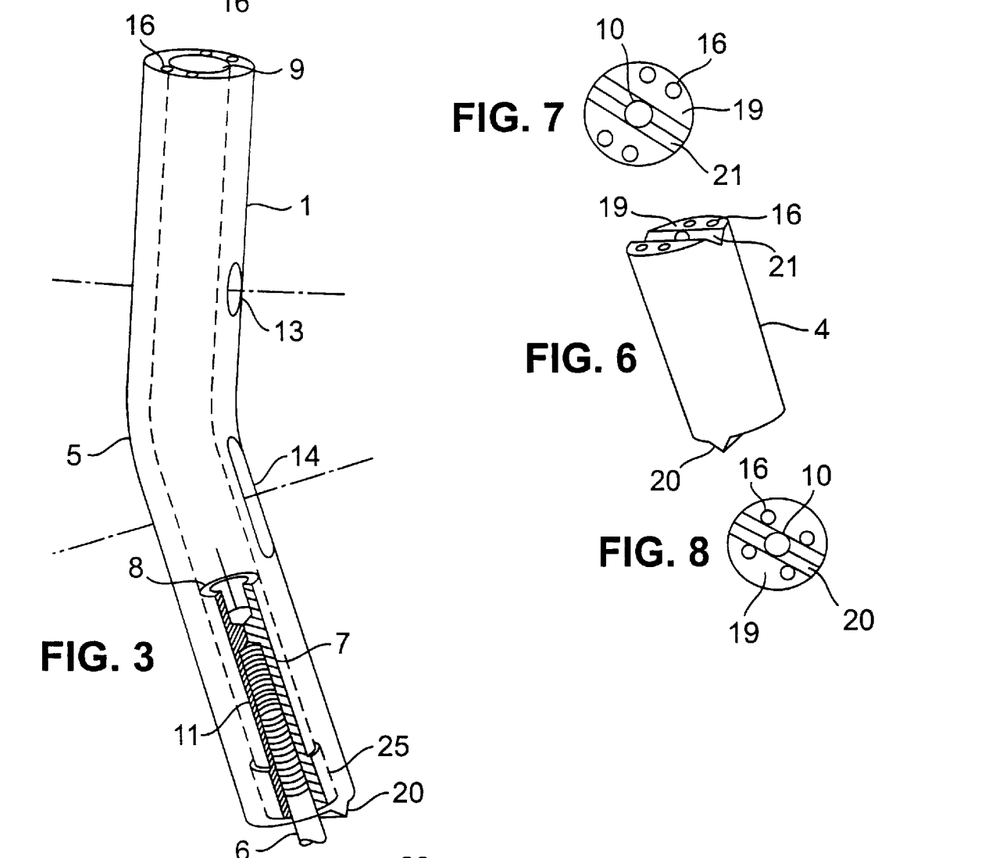
FIG. 3 is a perspective view of the upper end segment of the nail according to FIG. 1.
FIG. 6 is a perspective view of the first intermediate segment of the central portion of the nail adjacent to the upper end segment, of the nail according to FIG. 1.
FIG. 7 is a top plan view on the segment according to FIG. 6.
FIG. 8 is a bottom plan view on the segment according to FIG. 6.
Figure 4:
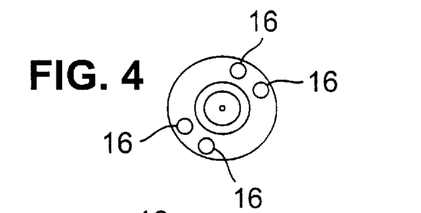
FIG. 4 is a top plan view on the segment according to FIG. 3.
Figure 5:
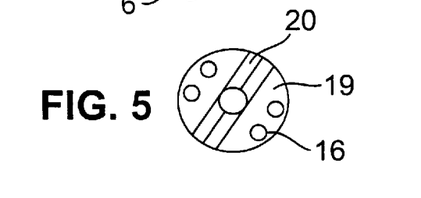
FIG. 5 is a bottom plan view on the segment according to FIG. 3.

As can be seen from FIGS. 3–5 the upper end segment 1 comprises a hollow tube having a bend 5 in order to better conform to the anatomical situation. In the lower part of the segment 1 a wire 6 is fixed in a rotatable nut 7. Nut 7 is seated on a retaining nut 25, inserted in a threaded socket at the bottom of a channel 9 which extends through the upper end segment 1.

Referring to FIGS. 6–14, each of the intermediate segments 4 is formed with a hole or channel 10 which may have a diameter of 0.5–4.0 mm, preferably 1–3 mm. The wire 6 extends through these channels and, as shown in FIG. 15 is anchored in the lower segment 3 by any suitable means; as for example by a suitable adhesive or by threading the socket with a thread having a hand selected appropriately with respect to the hand of the threads in nut 7. Thus when nut 7 is rotated, as by means of a suitable tool inserted in hexagonal socket 8, wire 6 is drawn upwardly through the central opening 11 of nut 7, thereby exerting a compressive force on the segments 4, pulling them together to adopt a rigid configuration. If desired, a cable may be used in place of a wire.

The end portions 19 of said segments 4 abutting against each other are designed in such a way, e.g. by sloping the surfaces of the contacting ends, that the device—when it is tightened to its rigid conformation—adopts a pre-determined shape. In order to prevent rotation of the single segments 4 with regard to each other (which would render alterable the pre-determined configuration) the lower surfaces of the segments are provided with projections 20 and the upper surfaces with corresponding slots or channels 21.

Figures 9, 10, 11, 12, 13, 14, 15:
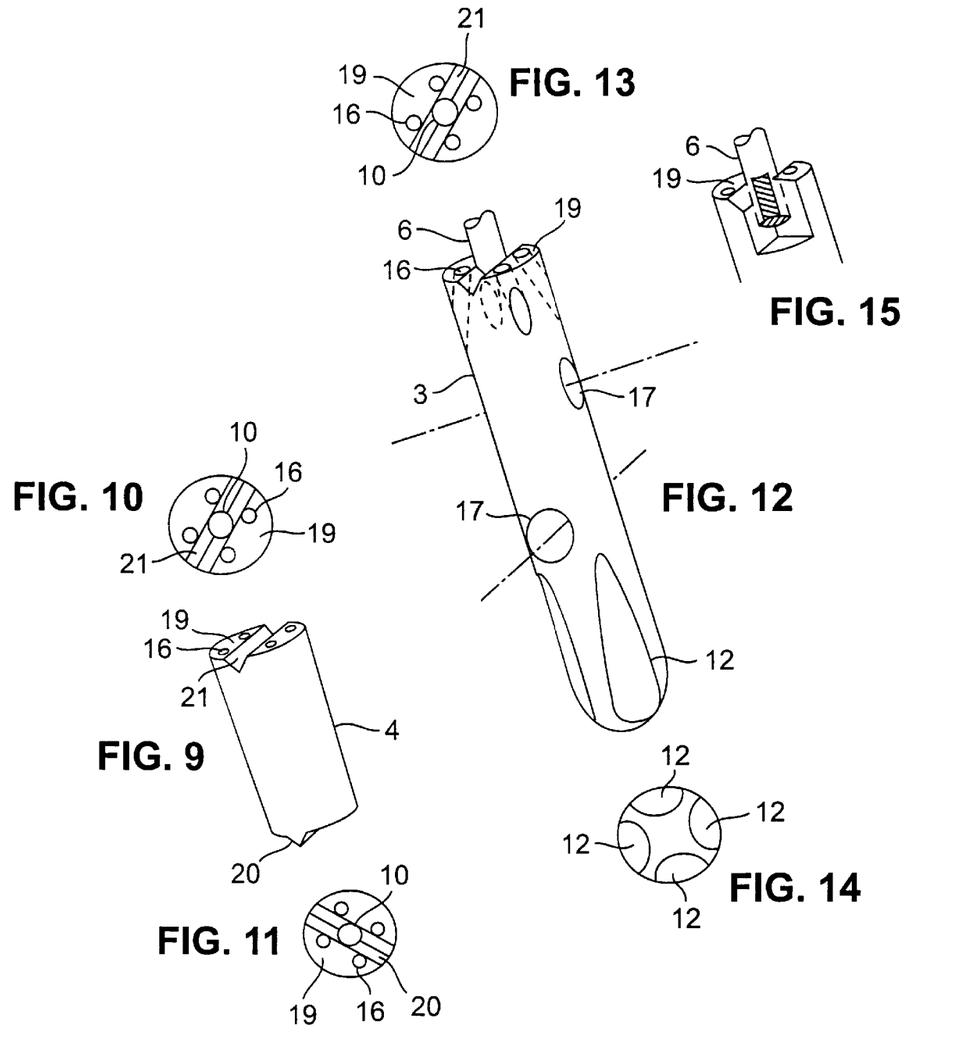
FIG. 9 is a perspective view of the second intermediate segment of the central portion of the nail according to FIG. 1.
FIG. 10 is a top plan view of the segment according to FIG. 9.
FIG. 11 is a bottom plan view on the segment according to FIG. 9.
FIG. 12 is a perspective view of the lower end segment of the nail according to FIG. 1.
FIG. 13 is a top plan view on the segment according to FIG. 12.
FIG. 14 is a bottom plan view on the segment according to FIG. 12.
FIG. 15 is an enlarged detail of FIG. 14.

As shown in FIGS. 12 and 14 the lower end segment 3 is provided with essentially longitudinal cut-outs 12 with sharp edges. This measure confers the additional function of a manual reamer to the device.

As shown in FIG. 4 upper segment 1 is further provided with a proximal locking hole 13 and a proximal locking slot 14, and segment 3 (FIG. 12) is provided with two distal locking holes 17, to receive locking bolts or pins (not shown).

The segments of this device according to the invention may also be provided with holes 16 running generally parallel to the longitudinal axes of the segment. These holes 16 accommodate locking wires 15. The number and arrangement of the holes and wires 16, 15 can vary; preferably four wires, symmetrically arranged are used. The distal tip of the wire which is to be driven into the bone is rounded as shown in FIG. 2. Locking wires such as wires 15 can be used along with locking bolts or pins.

Figure 15A:
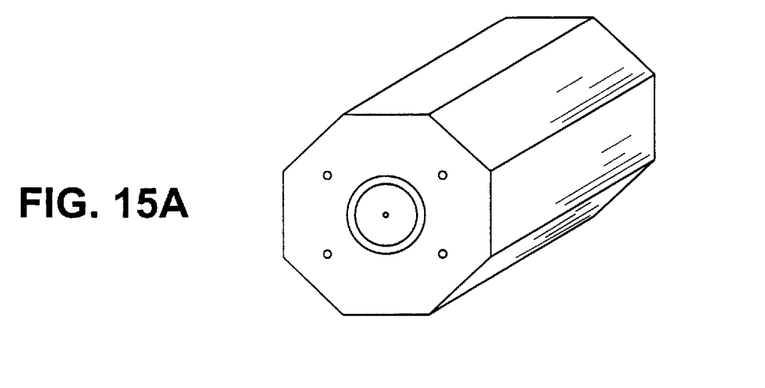
FIG. 15A is a perspective view of a segment having a polyhedral or prismatic shape.
Figure 15B:
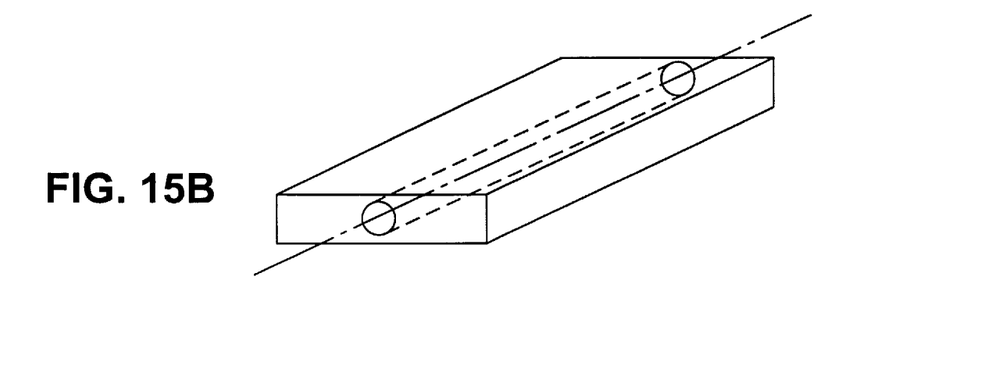
FIG. 15B is a perspective view of a segment having a flattened shape.
Figure 15C:
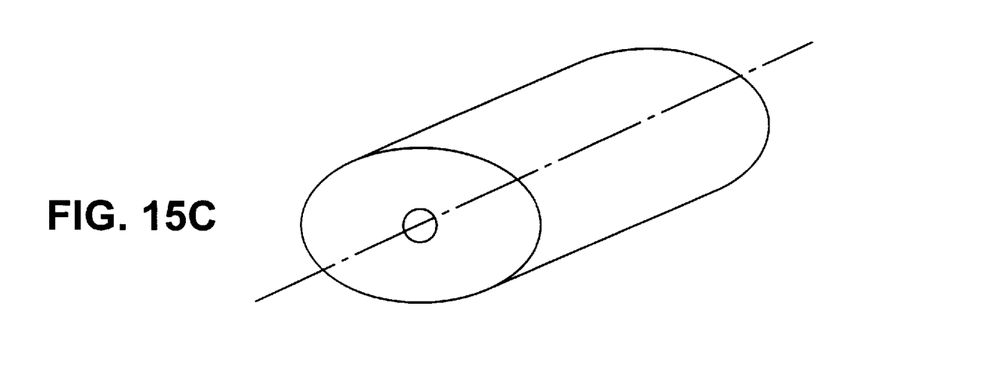
FIG. 15C is a perspective view of a segment having an oval shape.
Figure 15D:
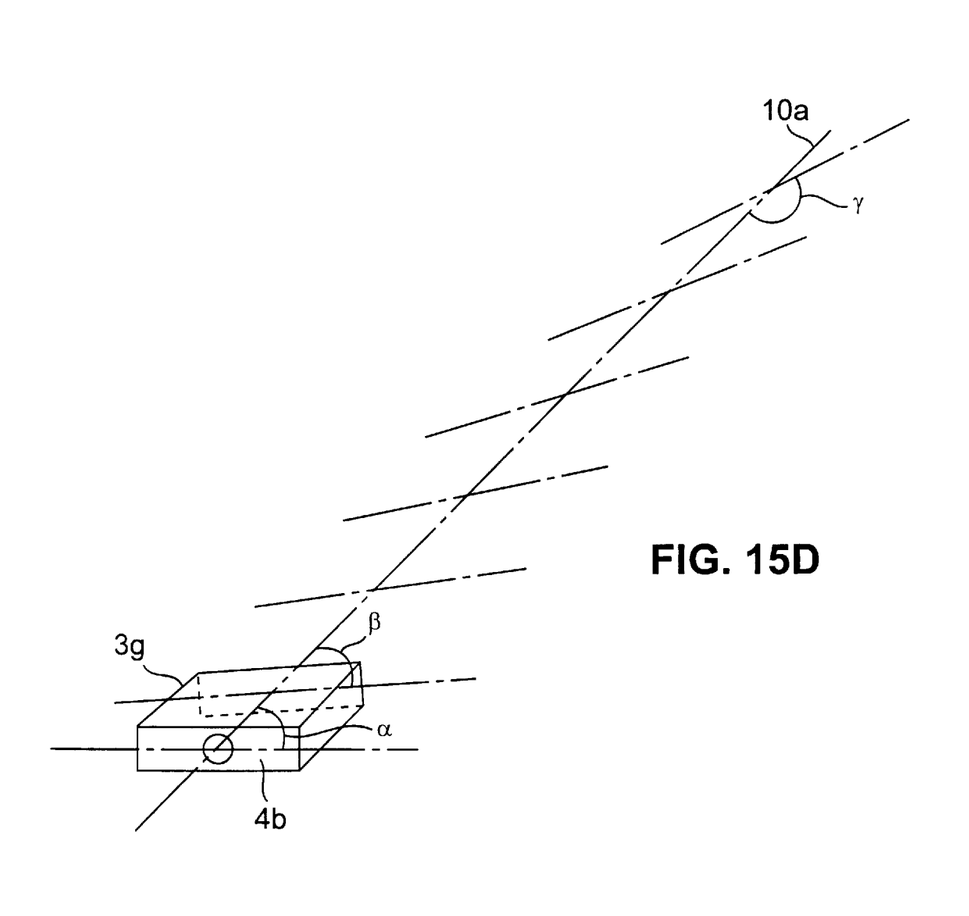
FIG. 15D shows schematically a nail according to the invention comprising segments which are helically twisted.

Although the cross section of the segments is shown as circular, it may be given any desired shape; for example it may be flattened (FIG. 15B) or oval (FIG. 15C) in shape. The segments may take the form of polyhedrons, for example prisms (FIG. 15A). The segments may have a clover leaf, triangular, square, rectangular or asymmetrical cross section. In certain cases one or more of the segments may be given a helical configuration. This is illustrated in FIG. 15D where segment 3g is helically curved so that the angle α between the mid line of the front end 4b and the axis 10a of the nail is different from the angle β between the mid line of the rear end 4d and the axis 10a. The overall helical rotation between one end of the device and the other, i.e. between α and the angle γ of the most remote segment as shown in FIG. 15D may be 30°–500°.

Figure 15E:
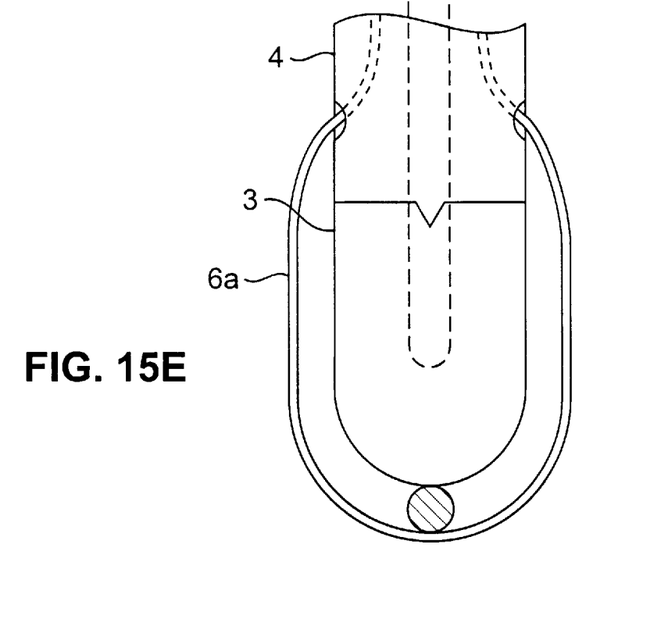
FIGS. 15E and 15F show a nail according to the invention having a wire extending in a loop beyond the distal end of the nail, the wire extending from the distal segment in FIG. 15F and from the segment adjacent the distal segment in FIG. 15E.
Figure 15F:
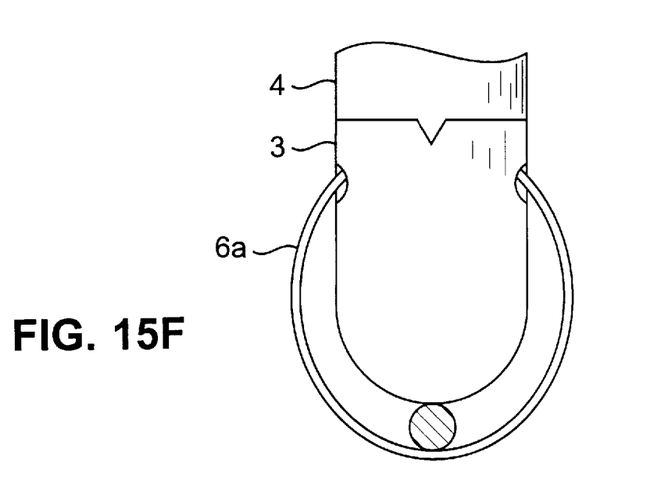

In place of a simple wire as shown in FIGS. 15E and 15F, a loop 6a may be formed, running the wire 6 out through an opening in the lower end segment 3 (FIG. 15F) or its immediate neighboring segment 4 (FIG. 15E) and back through a similar opening to form a loop at the end of the nail which may be used to engage a securing bolt in the manner described in U.S. Pat. No. 5,034,012. The return end of the wire is carried upwardly and secured in nut 7.

The way in which the invention may be used is believed clear from the foregoing description. However, purely for illustration, its use as an intramedullary nail in the treatment of a fracture of the diaphysis of the humerus will be described.

The fractured bone is first aligned sufficiently so that the medullary canal of the main proximal fragment is roughly aligned with the medullary canal of the main distal fragment. This ensures that device which is inserted through the first main fragment finds medullary canal of the second main fragment.

An insertion site is then chosen which is anatomically desirable so as to avoid interference with joints, growth plates and soft tissue. At insertion site, a pathway through skin and soft tissue is created. The underlying bone is exposed and an opening in the bone at this site through to the medullary canal is made.

In its flexible state and with its peripheral wires retracted as shown in FIG. 1, the device is introduced and fully inserted into the medullary canal through the opening at the insertion site. The device is then transformed into its rigid state, while keeping the peripheral wires in the retracted form. This is done by rotating nut 7 clockwise with a suitable tool (e.g. a screwdriver with a flexible shaft) which enters proximal part 1 via channel 9. This causes central wire 6 to be pulled into nut 7, thereby exerting a compressive force on segments 4 which are pulled together and adopt a rigid position with respect to each other.

To secure the bone fragments to the device so that the bone can be stabilized, the device can then be locked with bolts proximally, distally or both if desired. To do this, a locking bolt is placed through both bone and device (through hole 13, slot 14, hole 17 or any combination of these three). Precise aiming through these holes is done either freehand (with the aid of an image intensifier) or with an aiming device attached to proximal part 1 of nail.

A space between the two main bone fragments can be reduced by locking the device with bolts through at least one distal hole 17 in combination with slot 14. After implantation and during normal function of the arm, compressive forces are applied to the humerus, thus allowing the locking screw to slide along slot 14 and causing the fracture to close on its own.

If desired, peripheral wires 15 can be extended out of distal part 3, as shown in FIG. 2, to stabilize the fragment in rotation. To handle peripheral wires 15, a suitable instrument at top of proximal part 1 is used to push or tap peripheral wires 15 until they protract sufficiently (as seen using an image intensifier) at other end of bone and into (or at) the inner cortex.

Excess wires at top of proximal part 1 are cut off. Wires 15 can be cut flush to top end of proximal part 1. The soft tissue and skin are closed.

When and if it is desired to remove the nail, the wires 15 are pulled back until the wire ends are positioned inside the holes 16 and do not protrude out of distal part 3.

The nail is then made flexible by rotating nut 7 counterclockwise with a suitable tool which enters proximal part 3 via hole 9. This causes central wire 6 to be pushed out of nut 7, thereby releasing the compressive force on segments 4. The nail is pulled out of the medullary canal, even if ends of peripheral wires 15 have not been retracted into holes 16. Due to the elastic nature of the peripheral wires 15, there is a spring effect during removal from the medullary cavity which causes part of peripheral wires extending (protracting) out of distal part 3 to deform inwards. This elasticity of wires 15 avoids damage to inner cortex of medullary canal. The soft tissue and skin are then closed.

Figure 16:
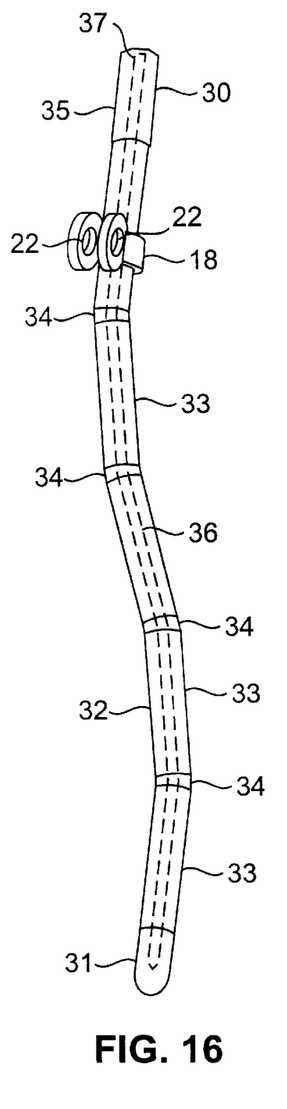
FIG. 16 is a perspective view of a spinal fixation device according to the invention.

As noted above, devices according to the invention may be used for applications other than intramedullary nailing. A spinal fracture device is illustrated in FIG. 16. This device comprises an upper end segment 30, a lower end segment 31 and a central portion 32 comprising a plurality of longitudinally arranged intermediate segments 33. In addition, the spinal fracture device comprises small wedge shaped segments 34 between the intermediate segments 33. The internal structure of the segments of the device of FIG. 16 may be similar to that shown in FIGS. 1–15, i.e. the upper end segment may have a nut 35, with an internal opening 37, corresponding to the nut 7 of FIG. 4 and a wire or cable 36 may extend through the intermediate segments to the lower end segment 31 for tightening the device in the manner described above in connection with FIGS. 1–15. The wedge shape of elements 34 leads to a bent configuration of the spinal fixator when it is tightened by means of rotatable nut 35 and non-rotatable wire 36 fixed to lower end segment 31.

The spinal fixator may also be provided with one or more clips 18 with through-holes 22 for receiving pedicle screws or hooks to be anchored in the bone.

Figure 17:
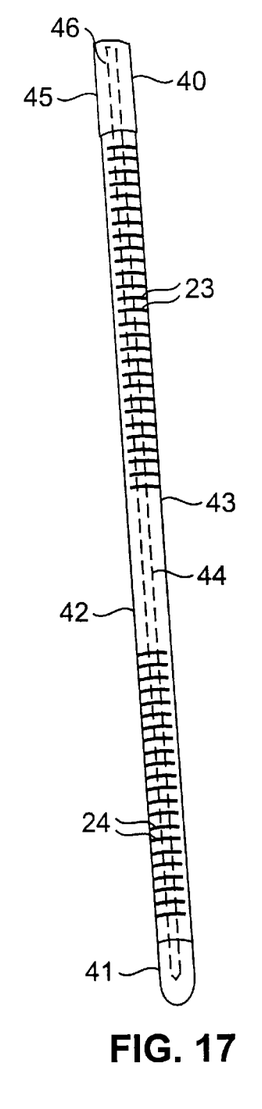
FIG. 17 is a perspective view of another embodiment of a nail according to the invention in the flexible state.
Figure 18:
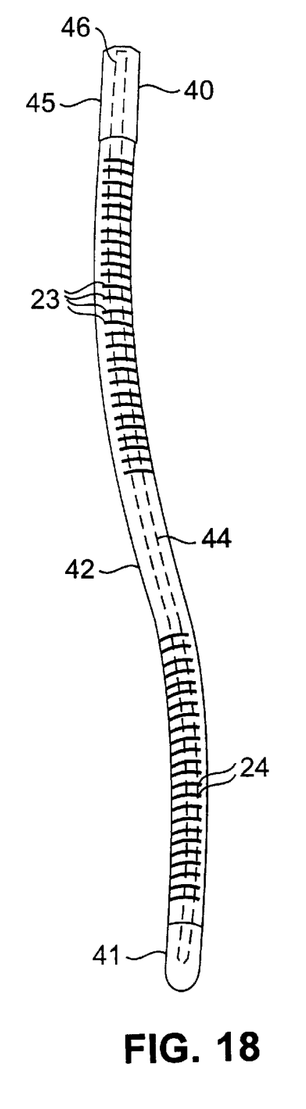
FIG. 18 is a perspective view of the nail of FIG. 17 in the stiffened state.
Figure 19:
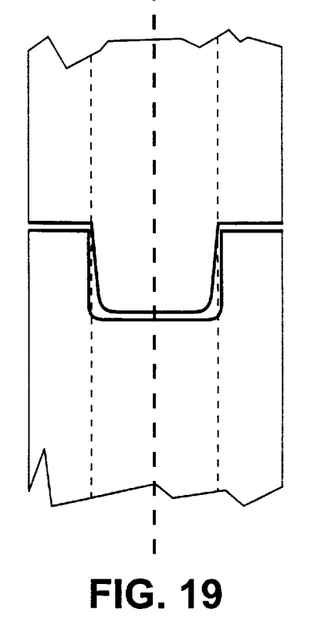
FIGS. 19–30 are additional views of pairs of segments in a nail in the flexible state according to the invention, illustrating a number of shapes which the abutting ends of adjacent segments can have.
Figure 20:
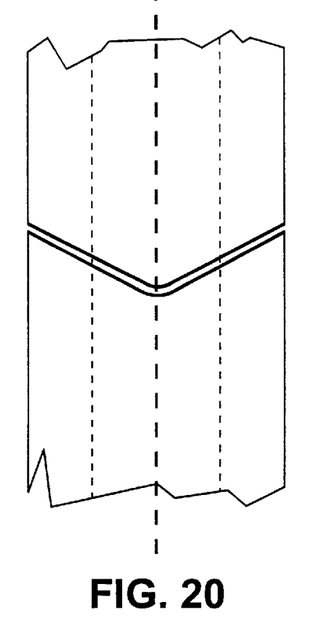
Figure 21:
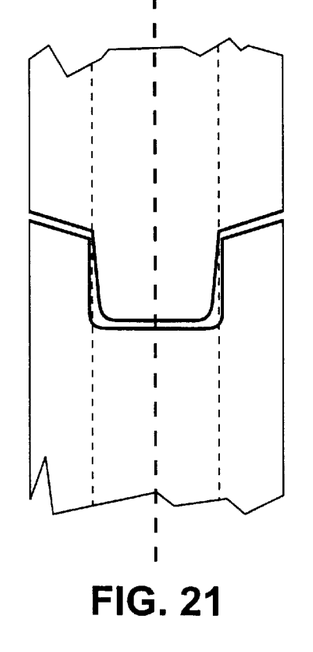
Figure 22:
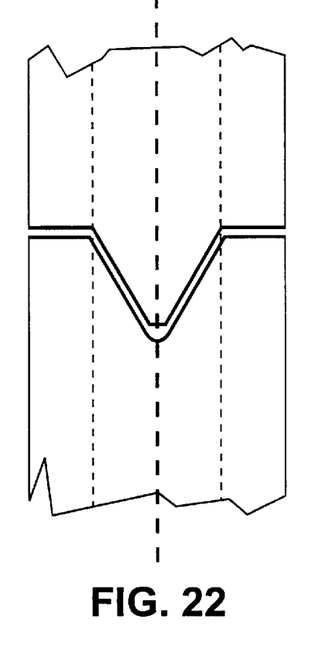
Figure 23:
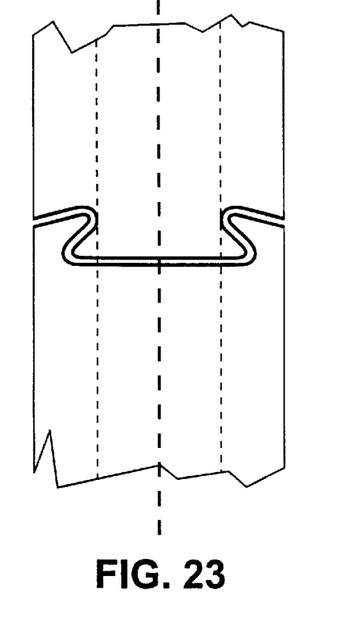
Figure 24:
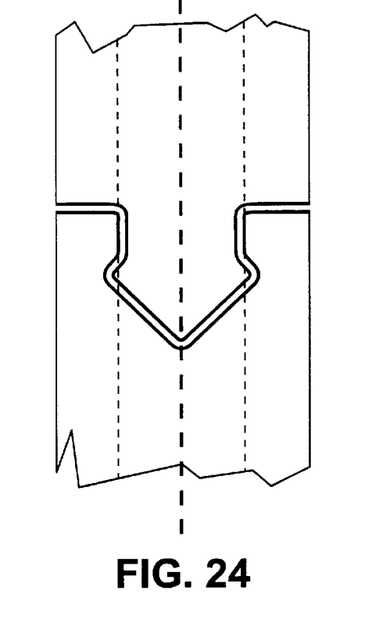
Figure 25:
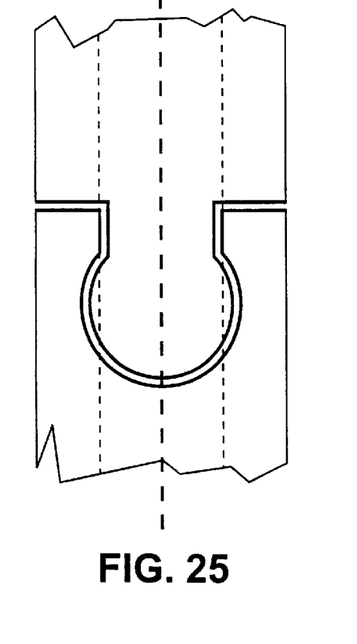
Figure 26:
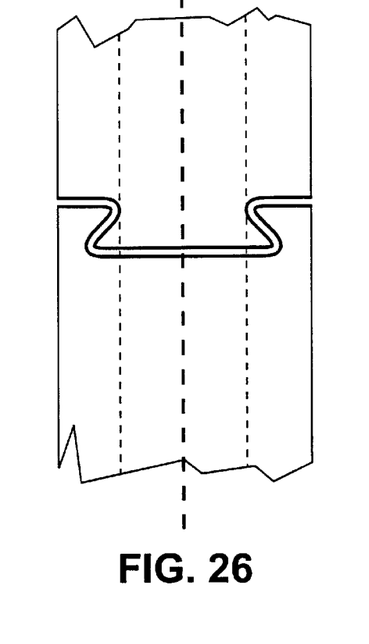
Figure 27:
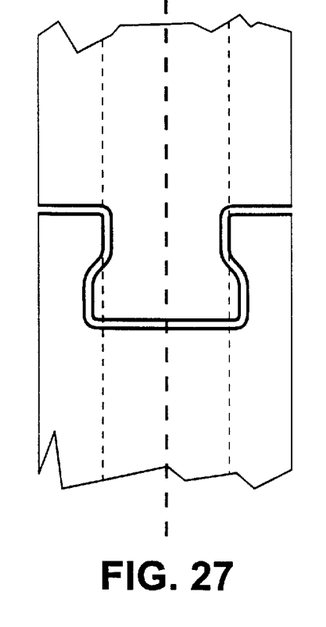
Figure 28:
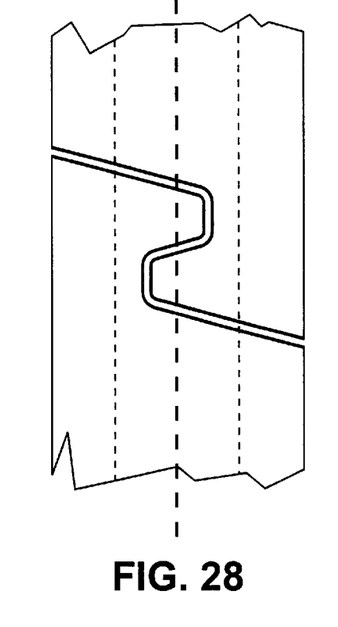
Figure 29:
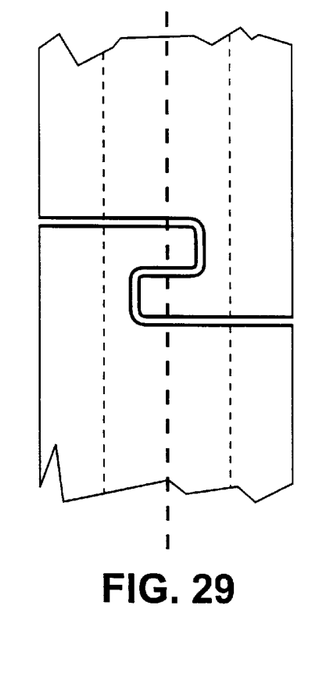
Figure 30:
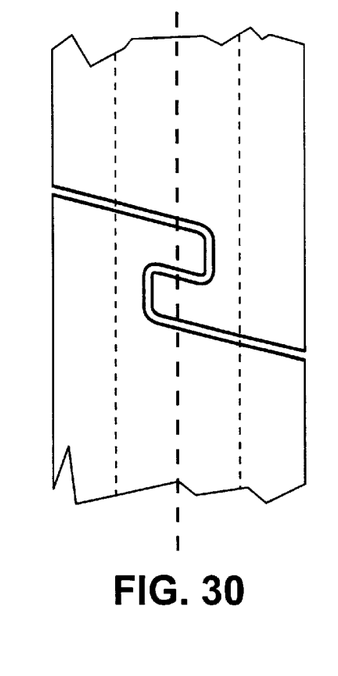

An alternative embodiment of the alignment or fixation device of the invention is shown in FIGS. 17–18. The device of FIG. 17 has essentially the same elements as the device according to FIG. 1, i.e. an upper end segment 40, a lower end segment 41 and a central portion 42. However in this case the central portion comprises a hollow tube 43. In place of distinct segments the tube 43 has a plurality of cuts 23,24. These cuts run circumferentially for approximately 180° to 350°, typically 300°. A central wire or cable 44 is fixed in lower end segment 41 and is threaded in a nut 45 having an internal opening 46, in a manner similar to the structure of FIG. 1. Several groups of cuts may be made having different circumferential positions. Thus, in FIG. 17 the upper group of cuts 23 is positioned on the right side and the lower group of cuts 24 is positioned on the left side of the tube. By this expedient it is possible to confer a pre-determined configuration to the device which it will assume upon tightening in a manner similar to that of the embodiment of FIG. 16, i.e. by rotating nut 44 from the outside with a suitable wrench. The pre-determined shape of the stiffened device is represented in FIG. 18, where the upper and lower parts are bent in different directions due to the different orientation of the cuts 23 and 24. By applying additional groups of cuts with selected orientations, it is possible to obtain a wide range of pre-determined shapes of the device upon tightening.

In using the device according to the invention as a spinal fixator, the following technique may be employed, illustrating correction of a spinal fracture or deformation using a dorsal approach.

First steps are taken to ensure that pre-determined shape of the stiffened device corresponds to desired shape of the spinal column. For the device shown in FIG. 16, this is done by inserting the appropriate number and shape of wedges 34 between the segments 33. For the device shown in FIGS. 17 and 18, the cuts 23 and 24 must result in the appropriate shape when the device is compressed. For both devices, the appropriate number of clips 18 must be put on the device and located in the appropriate positions along the length of the device.

The skin is then opened at the spinal column dorsally and soft tissue cleared away if necessary. The device, in the flexible state (e.g. FIG. 17) is placed in the desired position on the spinal column and secured to the spinal column as by placing screws through holes 22 of clips 18 and into the pedicles of the vertebral bodies. Since the device is in the flexible state, all screws should reach the pedicles by simple deformation of the device in the appropriate direction.

The device is stiffened by rotating the nut clockwise with a suitable tool (e.g. a wrench). This causes the central wire to be pulled up into the nut, thereby exerting a compressive force on intermediate segments (FIG. 16) and between cuts 23 and 24 (FIGS. 17, 18). During stiffening, the device takes on a pre-determined shape, corresponding to the normal anatomy of the spinal column and, since the device is secured to the spinal column, the spinal column also adopts this pre-determined anatomical shape.

The devices according to the invention may be made of any appropriate material, depending on the purpose to be served. They may be made of metals, for example an appropriate stainless steel or titanium or of plastic or plastic-composite.

While the foregoing description and drawings represent the preferred embodiments of the present invention, it will be obvious for those skilled in the art that various changes and modifications may be made therein without departing from the true spirit and scope of the present invention.

What is claimed is:

1. An osteosynthetic alignment or fixation device comprising an upper end segment, a lower end segment and a plurality of intermediate segments, each of said segments having upper and lower ends and a longitudinal axis, connecting means joining said segments end to end and tightening means for pressing said segments together into a rigid configuration, wherein the contours of the abutting ends of at least two of said segments are preselected for congruence so that when tightened the device is able to assume, at least for said at least two segments, only one single shape independent from the surrounding medium.

2. The device claimed in claim 1, wherein said shape corresponds to a longitudinal body having a straight central axis.

3. The device claimed in claim 1 wherein at least two of said segments are cylinders.

4. The device claimed in claim 3 wherein at least two of said segments are polyhedrons.

5. The device claimed in claim 4 where at least two of said segments are prisms.

6. The device claimed in claim 1, wherein at least some of said upper and lower ends of said segments have contacting surfaces substantially orthogonal to said longitudinal axis.

7. The device claimed in claim 1, wherein an end portion of at least one segment is provided with a substantially planar contacting surface having an inclination with respect to said longitudinal axis other than orthogonal.

8. The device claimed in claim 1, wherein an end of each of said segments is provided with a structured surface matching a structured surface of an abutting segment.

9. The device claimed in claim 1, wherein at least two of said segments are at least partially interlinked to each other.

10. The device claimed in claim 1, wherein said segments are provided with a longitudinal channel, the channel of each segment communicating with channels of adjacent segments, said connecting means being positioned in said channels.

11. The device claimed in claim 10, wherein said segments are each provided with at least two substantially parallel channels.

12. The device claimed in claim 10, wherein said channels have a circular cross section.

13. The device claimed in claim 12 wherein the channels have a diameter of 0.5–4.0 mm.

14. The device claimed in claim 13 wherein the channels have a diameter of 1 to 3 mm.

15. The device claimed in claim 1 wherein said connecting means is a wire.

16. The device claimed in claim 1 wherein the connecting means is a cable.

17. The device claimed in claim 1, wherein one of said intermediate segments near to said lower end segment is provided with at least two holes, said device further comprising a wire extending through said two holes and forming a loop at the end of said lower end segment.

18. The device claimed in claim 1, wherein the lower end segment is provided with at least two holes, said device further comprising a wire extending through said two holes and forming a loop at the end of said lower end segment.

19. The device claimed in claim 1, wherein all of said segments have a flattened cross section orthogonal to said longitudinal axis.

20. The device claimed in claim 19, wherein the segments have an oval cross section.

21. The device claimed in claim 19, wherein the flattened cross section is helically twisted around said longitudinal axis by 30°–500° over the entire length of the device.

22. The device claimed in claim 21 wherein the device is twisted by 30° to 150°.

23. The device claimed in claim 1, wherein at least one of said intermediate segments is made of non-metallic material.

24. The device according to claim 1 wherein at least one of the end segments is made of non-metallic material.

25. The device claimed in claim 1 wherein said segments are provided with channels at their peripheries, one of said segments being provided with outlets for said peripheral channels.

26. The device claimed in claim 1, wherein the longitudinal axis of said lower end segment is inclined with respect to the longitudinal axis of said intermediate segments.

27. The device claimed in claim 1, wherein said lower end segment is provided with substantially longitudinal cut-outs with sharp edges.

28. The device claimed in claim 1, wherein the device is provided with a proximal locking aperture.

29. The device claimed in claim 1, wherein the device is provided with a distal locking aperture.

30. An osteosynthetic longitudinal alignment or fixation device comprising a hollow tube having a wall and a longitudinal axis and partial cuts in said wall transverse to said axis, said cuts being positioned to render said tube flexible and said device further comprising a tightening means for compressing said cuts, at least along a section of the device, into a rigid longitudinal conformation of only one single shape independent from the surrounding medium.

31. The device claimed in claim 30 comprising a plurality of groups of cuts, said groups being displaced from one another around the periphery of the tube.

* * * * *